United States Patent [19]

Chang et al.

[11] Patent Number: 4,596,774

[45] Date of Patent: Jun. 24, 1986

[54] METHOD OF PREPARING MURINE MONOCLONAL ANTIBODIES AGAINST CELL-FREE PRODUCTS OF ACTIVATED HUMAN T-LYMPHOCYTES

[75] Inventors: Tse-Wen Chang; Nancy T. Chang, both of Paoli, Pa.

[73] Assignee: Centocor, Inc., Malvern, Pa.

[21] Appl. No.: 547,941

[22] Filed: Nov. 2, 1983

[51] Int. Cl.[4] .................. C12P 21/00; C12N 5/00; C12N 5/02; C12R 1/91
[52] U.S. Cl. ..................................... 435/68; 435/240; 435/241; 435/948; 530/387; 530/806; 530/351
[58] Field of Search ............. 260/112 R; 435/68, 240, 435/241, 948

[56] References Cited

U.S. PATENT DOCUMENTS

| | | | |
|---|---|---|---|
| 4,401,756 | 8/1983 | Gillis | 435/68 |
| 4,411,992 | 10/1983 | Gillis | 435/68 |
| 4,411,993 | 10/1983 | Gillis | 435/68 |
| 4,468,460 | 8/1984 | Kumamoto | 435/240 |

FOREIGN PATENT DOCUMENTS 0047629  4/1980  Japan .................. 435/240

OTHER PUBLICATIONS

Neta et al, from *Lymphokines* vol. 2, Edgar Pick, Editor, pp. 296–301, 1981.

*Primary Examiner*—Thomas G. Wiseman
*Assistant Examiner*—Robin Lyn Teskin
*Attorney, Agent, or Firm*—Hamilton, Brook, Smith & Reynolds

[57] ABSTRACT

A method of preparing simultaneously monoclonal antibodies specific for different cell-free products of activated human T lymphocytes is disclosed. Human T cells are activated in a medium supplemented with mouse serum rather than conventional calf serum. A supernatant prepared from the activated T cells is used to immunize mice. The dominant immunogens in the supernatant are the cell-free products of human T lymphocytes. The yield of hybrid cells which produce products reactive with cell-free products of human T lymphocytes is enhanced by injecting the immunized mice with a supernatant from mitogen-activated murine splenocytes. In addition, a novel radioimmunoadsorbent assay for screening hybrids to detect production of monoclonal antibodies reactive with cell-free products of human T lymphocytes is disclosed.

13 Claims, 8 Drawing Figures

METHOD OF PREPARING MURINE MONOCLONAL ANTIBODIES AGAINST CELL-FREE PRODUCTS OF ACTIVATED HUMAN T-LYMPHOCYTES

FIELD OF THE INVENTION

This invention is in the fields of immunology and cell biology. The invention pertains to a method of preparing simultaneously monoclonal antibodies specific for different cell-free products produced by activated human T lymphocytes.

BACKGROUND OF THE INVENTION

Among the various cell types involved in immune responses, T lymphocytes play the major regulatory roles. While T cells interact with other leukocytes by direct contact involving cell surface molecules, they also secrete a large variety of regulatory factors. Partially or highly purified preparations of some of these factors from various sources have been shown to mediate or regulate distinct immune responses in in vitro or in vivo experimental systems. See, for example, David, J. R. and Remold, H. G. (1976) In: *Immunology of the Macrophage,* Ed. D. S. Nelson (Academic Press, NY), p. 401.

When T cells are placed in culture and stimulated with polyclonal T cell mitogens, they secrete into the culture medium antigen-nonspecific factors (lymphokines) of a broad spectrum of activities associated with T cell functions. Morley, J., et al. (1978) In: *Handbook of Experimental Immunology,* Ed. D. M. Weis (Blackwell Scientific Publications, Oxford), Chapter 27; Rocklin, R. E. et al. (1980) *Adv. Immunol.* 29, 55; Oppenheim, J. J. (1981) In: *Cellular Functions in Immunity and Inflammation,* Eds. J. J. Oppenheim et al. (Elsevier, NY), p.259. As a result, this "activated T cell supernatant" has been used as the source of the various factors. However, because the biological assays for many factors are often time consuming and imprecise, separation of the factors and characterization of their structure and function are formidable tasks. A typical problem has been that a given preparation of T-cell factors often contains several distinct biological activities.

Monoclonal antibody methodology has provided an attractive means to analyze the various components in the activated T cell supernatant. Once monoclonal antibodies are obtained, they can be used to define, to quantitate, and most importantly, to isolate specific molecules in the activated T cell supernatant mixture. This approach has proved very powerful in the analysis of crude antigen mixtures; the most notable example is the studies on surface differentiation antigens and alloantigens of leukocytes. Brodsky, F. M. et al. (1979), *Immunol. Rev.* 47, 3; Lemke, H. et al. (1979) *Immunol. Rev.* 47, 175; Kung, P. C. et al. (1979) *Science* 206, 347; Ledbetter, J. A. and L. A. Herzenberg (1979) *Immunol. Rev.* 47, 63.

Monoclonal antibodies against two T cell factors of interest have been prepared. Gillis, S. and C. S. Henney (1981), *J. Immunol.* 126, 1978; Stadler, B. M. et al. (1982), *J. Immunol.* 128, 1620; Smith, K. et al. (1983), *J. Immunol.* 131, 1808. In most instances partially purified factors have been used as the immunogens for preparation of hybrid antibody-producing cells and the hybrids have been screened in assays for inhibition of the activity of the various factors. However, the partial purification of individual factors of activated human T-lymphocytes requires a great deal of effort. Further, this approach is useful only for known factors.

SUMMARY OF THE INVENTION

This invention pertains to a method of preparing simultaneously monoclonal antibodies which are specific for different cell-free products produced by cultured activated human T lymphocytes. According to the method of this invention, a supernatant from mitogen-activated human T lymphocytes is used to immunize mice against the cell-free products of activated human T cells. The supernatant is prepared by incubating human cells in a culture medium supplemented with mouse serum and activating the cells with a mitogen. The mouse serum supports mitogen activation of human T cells better than the conventional fetal calf serum. Further, mouse serum permits the preparation of a supernatant in which the dominant immunogeneic substances in mice are the components of activated human T cells.

After mice are immunized with the supernatant, prior to harvesting the spleen for fusion, the mice are injected with a supernatant from mitogen-activated murine splenocytes. The spleen cell supernatant increases the yield of hybrid cells which produce monoclonal antibodies reactive with activated T cell substances.

Hybrids which produce antibodies against cell-free substances of activated T cells are selected by a screening procedure. The screening procedure includes a radioimmunoadsorbent assay. An immunoadsorbent is formed by conjugating the cell-free product in the supernatant of the activated human T cells (the same supernatant preparation used to immunize the mice) to a solid phase. In a preferred mode, the radioimmunoadsorbent assay is performed by contacting the immunoadsorbent with hybrid supernatant and subsequently with a labeled second antibody against mouse immunoglobulin.

DETAILED DESCRIPTION OF THE INVENTION

Figure 1:
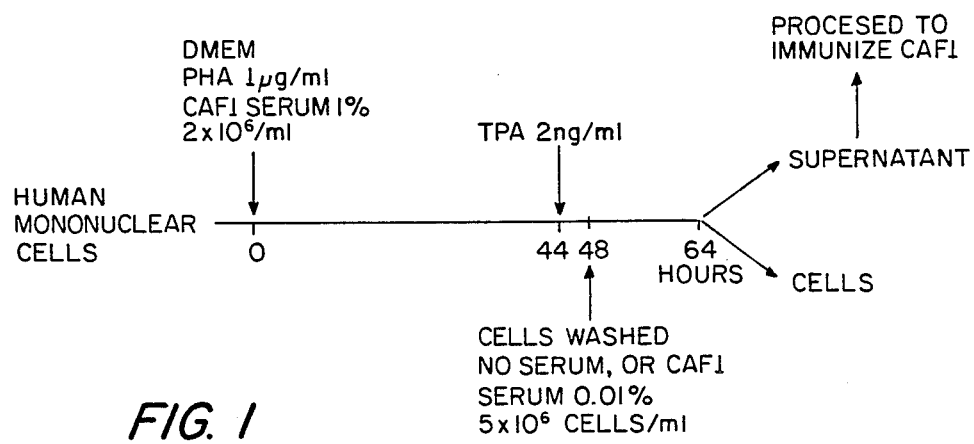
FIG. 1 outlines the method of preparing the antigen preparation, cell free products of activated human T lymphocytes.

This invention constitutes a method for the simultaneous preparation of monoclonal antibodies against cell-free molecules produced by mitogen-activated human T lymphocytes. Mitogen-activated human T lymphocytes produce a variety of hormone-like factors or lymphokines which are believed to mediate the immune response in vivo. These factors are thought to act in a microenvironment to influence and regulate various aspects of the immune response. The primary objective of this invention is to exploit monoclonal antibody technology as a means for discovering, isolating and characterizing regulatory factors produced by mitogen-activated human T lymphocytes.

In contrast to methods of the prior art, which have generally been directed to the production of monoclonal antibody against a particular factor produced by activated T lymphocytes, the method of this invention may be described as a "shotgun" approach. Rather than focusing on any particular factor or lymphokine generated by activated T cells, the methodology of this invention is aimed at the simultaneous production of monoclonal antibodies against a multiplicity of the factors present in a supernatant of activated human T lymphocytes. Once the antibodies are produced, they may be used to isolate and characterize the individual components of the T-cell supernatant.

For implementation of this approach, there are three broad requirements. The first requirement is a suitable antigen preparation, one in which the various factors of activated human T lymphocytes are present in sufficient amount to induce an immune response when injected into mice. Importantly, the factors should be the dominant immunogens in the preparation such that the immune response elicited in mice is directed predominantly toward the factors. The second requirement is an effective immunization procedure for eliciting the immune response against the various factors present in the immunogen preparation. The third requirement is a screening technique for selecting among a large number of hybrid cells those hybrids which secrete antibodies reactive with the factors of activated human T lymphocytes. The method of this invention satisfies each of these requirements.

The antigen preparation is a specially prepared supernatant from activated human T lymphocytes which is essentially devoid of contamination with exogenous substances, for example, antigenic substances of serum supplement or T cell inducer substances (e.g., mitogens). Because of this, the cell-free substances of activated T cell are the dominant immunogenic substances in the preparation.

To form the supernatant, human T lymphocytes are suspended in a suitable cell culture medium such as Delbecco's Modified Minimal Essential Medium (DMEM). A suitable source of T lymphocytes is peripheral blood mononuclear cells, but the T lymphocytes may be obtained from spleen, lymph node or other tissues. The cell culture medium, however, is supplemented with mouse serum rather than the conventional fetal calf serum. Preferably, the mouse serum is obtained from mice of the same strain as those which will later be immunized against the supernatant preparation.

The use of mouse serum in the preparation of a supernatant from activated human T cells designed to serve as an immunogen for mice minimizes antigen competition. Serum, especially heterologous serum, is itself immunogenic. When heterologous serum is present in an immunogen preparation, the immune response evoked against the preparation may be directed in large part against the components of serum rather than the desired antigen or antigens in an immunogen preparation. Because the immunogen preparation is to be used to immunize mice, the cell culture medium is supplemented with mouse serum in order to reduce antigen competition and to enhance the immunogenic response in mice against the factors of activated human T cells. Further, in order to eliminate an anti-allogeneic response against the components of mouse serum, the cell culture medium is supplemented with serum from mice of the same strain (syngeneic strain) as the mice chosen for immunization.

Unexpectedly, the use of mouse serum provides an additional advantage. Mouse serum was found to support the proliferative response of human T lymphocytes to mitogen better than calf serum. A much lower concentration of mouse serum is required for optimal stimulation of human T lymphocytes. This fact allows the preparation of "cleaner" supernatant. Additionally, it appears that the mouse serum enhances the production of factors associated with T-cell activation, as indicated by increased IL-2 production and thus provides a more enriched supernatant.

After the T lymphocytes are suspended in the mouse serum-supplemented medium, a mitogen is added to stimulate the cells. Phytohaemagglutinin A(PHA) is the preferred mitogen because it is a powerful stimulant of human T cells. To enhance the mitogen activation and the production of factors associated with activation the phorbol ester, subsequently, 12-O-tetradecanoyl phorbol 13-acetate (TPA) is added to the medium. In one embodiment optimal enhancement of PHA activation is achieved by adding the TPA at about 40 hours after the addition of PHA and exposing the cells to TPA for about 4 hours at a concentration of about 2 to about 20 ng/ml. Optimal enhancement may be determined by the ability of the resulting supernatant to induce Interleukin-2 production and to induce proliferation of normal peripheral blood mononuclear cells.

After exposure to TPA, the cells are separated from the medium, generally by centrifugation. The cells are washed thoroughly and re-suspended in a second medium which is serum-free. The cells are maintained in the serum-free medium, preferably for about 16 hours. Thereafter, the medium is separated from the cells to yield the supernatant. The resulting supernatant may be concentrated by reducing the water content and purified by dialysis. This supernatant constitutes the antigen preparation. As described infra, the supernatant is also used as the antigen in assays for initial screening of hybrid cells and mouse immune serum.

Although it is not clear how much of the total protein in the supernatant actually can be accounted for by the T-cell secretory factors, the fact that the mouse antiserum contained antibodies reactive with surface antigens of active and resting T cells suggests either that antigens on the cell surface can be shed into culture medium or that minute membrane fragments are released into medium from disintegrating dead cells. Also, intracellular components may be released into the culture medium from lysed cells. These substances certainly constitute a part of the "cell-free" activated T cell substance pool. However, when cells were not stimulated with PHA and TPA, much less cell-free protein could be harvested, suggesting material released from dead cells might not be the major components of the T cell supernatant. Another favorable indication was that most proteins in the T cell supernatant were in 10,000 to 50,000 daltons molecular weight range, wherein most known secretory T cell factors are.

Because there is the possibility that certain antigens in this supernatant are present in insufficient amounts to be immunogenic, it may be desirable to fractionate the substances of the T cell supernatant into several fractions according to molecular size or other criteria. The fractions could be used to immunize mice. Conceivably the chance of eliciting an immune response against components present in only small amounts will be increased.

The mice are immunized by conventional procedures, usually by an initial injection followed by periodic boosting injections of the activated T cell supernatant. However, just after the final boosting injection of the activated T cell supernatant, prior to harvesting the spleen cells for fusion, the mice are injected with a supernatant from mitogen-activated mouse spleen cells. The mitogen-activated supernatant from mouse spleen cells increases the yield of hybrid cells which produce products reactive with the cell-free factors from activated human T lymphocytes. When injection of the activated spleen cell supernatant is omitted, approximately 0 to 5 hybrids which produce reactive products result from the fusion of myeloma cells and spleen cells from two mouse spleens. In contrast, administration of the activated mouse spleen cell supernatant yields a 5 to 10-fold increase in the number of hybrid cells which produce products reactive with components of the activated T cell supernatant. Thus, it appears that the mouse spleen cell supernatant increases the number of antibody-producing splenocytes.

The supernatant from activated spleen cells is prepared in substantially the same manner as the supernatant from activated human T cells. Spleen cells are suspended at in a medium supplemented with mouse serum. Preferably, the concentration of spleen cells is about $5 \times 10^6$ cells/ml. The cells are exposed to PHA and subsequently to TPA for the same duration as in the preparation of the human T cell supernatant. However, the PHA concentration should be about 2-4 times greater and TPA concentration about 2-10 times less. The cells are removed from the medium and resuspended in a serum- and inducer-free medium. Thereafter, the medium is separated from the cells, concentrated and dialysed. The supernatant is then administered to the immunized mice.

The hybrids are screened by a solid phase immunoadsorbent assay, by flow cytometric analysis and other assays. The immunoadsorbent assay tests for reactivity of hybridoma products with the immunogen preparation, i.e., the cell-free products of the activated human T cell supernatant, and, accordingly, it is geared to detect hybrid products reactive with substances of activated T cells, regardless of whether the T cell products are secretory factors, intracellular components released from dead cells or molecules shed from the membrane. This assay permits selection from a large number of hybrids those which will be the subject of further study.

The immunoadsorbent assay is prepared by forming a solid phase immunoadsorbent by attaching cell free products from the activated T cell supernatant to a suitable solid phase. In order to ensure that the assay is sensitive for all or most of the products of activated human T lymphocytes, the immunoadsorbent must have a large overall capacity such that each of the various products of activated human T cells are attached to the solid phase in sufficient amounts. Toward this end the choice of the solid phase is crucial. A preferred solid phase is crosslinked agarose beads known as Sepharose-4B beads. The beads may be activated with cyanogen bromide to couple the activated T cell substances to the bead. Using these beads, immunoadsorbents may be constructed to detect hybrid products reactive with human T cell substances which account for only about 0.1% of the entire protein content of the T cell supernatant.

In its preferred embodiment, the radioimmunoassay is performed by contacting the immunoadsorbent with a hybrid supernatant and, after an appropriate time, separating the immunoadsorbent from the supernatant and then contacting the immunoadsorbent with a labeled antibody directed against mouse immunoglobulin (Ig). The immunoadsorbent is then separated from the unbound anti-mouse Ig antibody and the amount of label associated with the immunoadsorbent is determined. The label associated with the immunoadsorbent is an indication of the presence of reactive hybrid products in the hybrid supernatant.

The immunoadsorbent assay may be used as a first level screening technique to sort out hybrids of potential interest. The assay may also be used to screen subclones of hybrids selected on the basis of the original screen.

The identical assay may also be used to screen the serum of mice receiving the immunogen preparation to determine if an immune response against components of the activated T-cell supernatant has been raised in the mice. In this way spleens may be selected for fusion only from mice displaying an immune response. As a result, the likelihood of obtaining hybrids which produce antibodies against T-cell factors is increased.

After hybrids of interest are identified by the initial screening procedures, the hybrids may be further analyzed by testing for the biological effects of hybrid products, such as their effects upon lectin, allogeneic cell or virus induced proliferation of T-cells or their effects on cell mediated lysis. Further, the antibody products of the hybrids may be used in immunopurification techniques to isolate the specific substance in the supernatant of activated T cells with which they react.

The invention is further illustrated by the following Exemplification.

EXEMPLIFICATION

I. Preparation of cell-free products of activated human T lymphocytes

The method of preparing cell-free products of activated T lymphocytes, described in detail below, is outlined in FIG. 1.

Mononuclear cells from the peripheral blood of healthy adults were isolated by centrifugation on a discontinuous density gradient (Ficoll/diatrizoate sodium, d=1.077, from Pharmacia Chem. Co., Piscataway, NJ). Cells recovered from the interface were suspended at $2 \times 10^6$/ml in DMEM supplemented with nonessential amino acids, vitamins, and 1% normal mouse serum of CAF1 mice (Dutchland Labs., Denver, PA) and phytohaemagglutinin A (PHA, Burroughs-Wellcome, Research Triangle Park, NC) at 1 ug/ml, and incubated in 8% $CO_2$/92% air at 37° C. At 44 hours 12-O-tetradecanoylphorbol 13-acetate (TPA, from P-L Biochem., Milwaukee, WI) was added at a final concentration of 4 ng/ml. The cells were incubated for 4 additional hours before they were harvested. The medium was removed by centrifugation and the cells were washed three times with serum-free medium. They were then resuspended at $5 \times 10^6$ cells/ml in serum and protein-free DMEM for 16 hours. The culture supernatant was then filtered through a 0.22 u filter, added 1/5 volume of 0.5M sodium phosphate buffer (pH 7.4), transferred to dialysis tubes (6,000–8,000 M,W, cut off), concentrated 200 fold with carboxymethylcellulose (Aquacide I-A, Calbiochem., La Jolla, CA), and dialyzed against phosphate buffered saline (PBS, pH 7.4). Protein content was determined by a protein assay (Bio-Rad Labs., Richmond, CA). A typical preparation of 600 ml blood having about $1 \times 10^9$ mononuclear cells yielded about 1 mg protein.

The dialyzed activated T cell supernatant concentrate was used as the immunogen and as the reagent to screen the hybrids. In some preparations, 0.01% CAF1 mouse serum was included in the final medium. The serum provided carrier protein to minimize nonspecific attachment of cellular protein to the plastic culture flask.

Two criteria were used to determine the optimal conditions for stimulating human peripheral blood mononuclear cells (PBM's). These are: (1) the proliferation of the PBM's as measured by $^3$H-thymidine incorporation, and (2) the ability of the resulting supernatant to induce proliferation of fresh PBM's.

Because the activated T cell supernatant substance was to be used as an immunogen in mice, it was desirable to use mouse rather than fetal calf serum as supplement in the culture medium.

Figure 3:
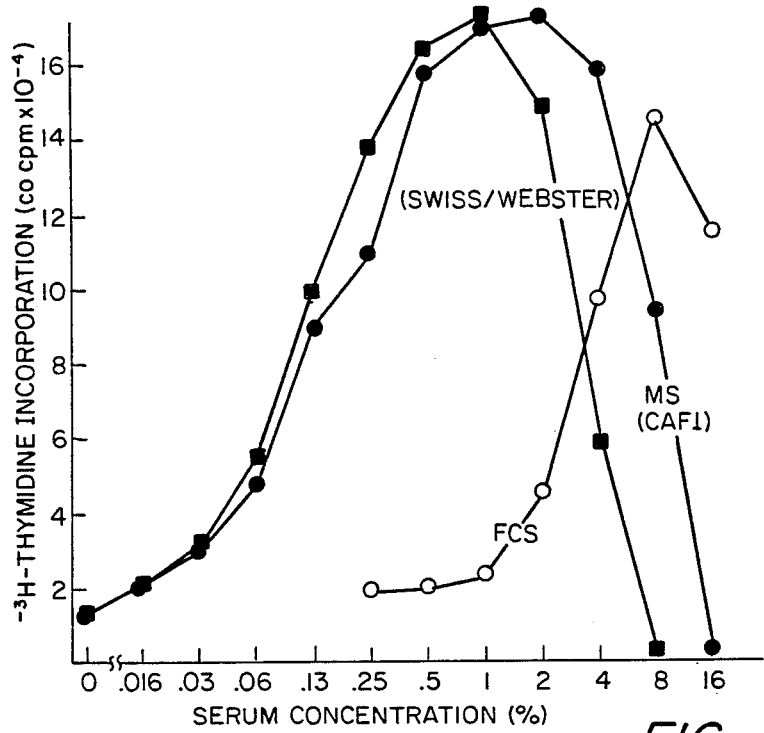
FIG. 3 shows the supportive effects of mouse serum and fetal calf serum on PHA induced proliferation of human mononuclear cells.

FIG. 3 shows the supportive effects of mouse and fetal bovine sera on PHA-induced proliferation of human mononuclear cells. Mouse sera (MS) were from normal mice of CAF1 (BALB/c X A). $2 \times 10^5$ human PBM's were incubated in 200 ul DMEM containing PHA (1 ug/ml) and varying concentrations of the sera in flat-bottomed wells of $8 \times 12$ microtiter plates. After incubating at 37° C. for 60–64 hours, 0.5 uCi $^3$H-thymidine in 50 ul was added to each well and cells were incubated for an additional 6 hours. The cells were harvested, washed, and lysed with a cell harvester (Microharvestor, Bellco Glass Inc., Vineland, NJ). The DNA retained by the filter was counted for $^3$H. Each number in the graph is the average of three determinations.

Surprisingly, normal mouse serum was found to support the proliferative response of human PBM's to PHA as well as or even better than fetal calf serum. Moreover, a much lower concentration of mouse serum was required than that of fetal calf serum for the optimal stimulation (FIG. 3). Based on the results, 1% mouse serum was used in the culture medium.

Also examined was the effect of TPA on the production of T cell factors. TPA has been shown to augment mitogen-induced secretion of immuno-factors such as IL-1, IL-2, IL-3 and γ-interferon. Vilcek, J. et al. (1980) In: *Biochemical Characterization of Lymphokines*, Eds. A. L. DeWeck et al. (Academic Press, NY), p. 323; Fuller-Farrar, M. L. et al. (1981), *Cell Immunol.* 58, 156; Mizel, S. B. and D. Mizel (1981), *J. Immunol.* 126, 834. Several parameters were examined: time point for addition of TPA, duration of TPA in culture, and the concentration of TPA. Testing for the activity of TPA to induce normal PBM's to proliferate, the following optimal parameters were established: (1) the best time for addition was around 40 hours from the beginning of culture, (2) the optimal duration of TPA was 4 hours, and (3) the effect of TPA reaches optimum at a concentration of 2 ng/ml; similar effects are seen at 5 or 10 ng/ml.

The PHA and TPA-induced T cell supernatant (produced by the method outlined in FIG. 1 and described supra) was compared to a supernatant of T cells induced by PHA alone for 2 days for their ability to induce proliferation of an IL-2 dependent long term human alloreactive T cell clone.

The IL-2 dependent clone was prepared by cloning PBM's that had been stimulated with allogenic PBM's, with the PHA/TPA supernatant prepared as in FIG. 1. The clone had been in culture for about 5 months. The PHA-activated supernatant was obtained from a culture of PBM's that were stimulated with PHA for 48 hours. (PHA was not removed.) In the experiment, $5 \times 10^5$ IL-2 dependent cells were incubated with varying concentrations of the two different supernatants for 3 days. $^3$H-thymidine incorporation was measured as described above. Numbers are the average of two determinations.

Figure 4:
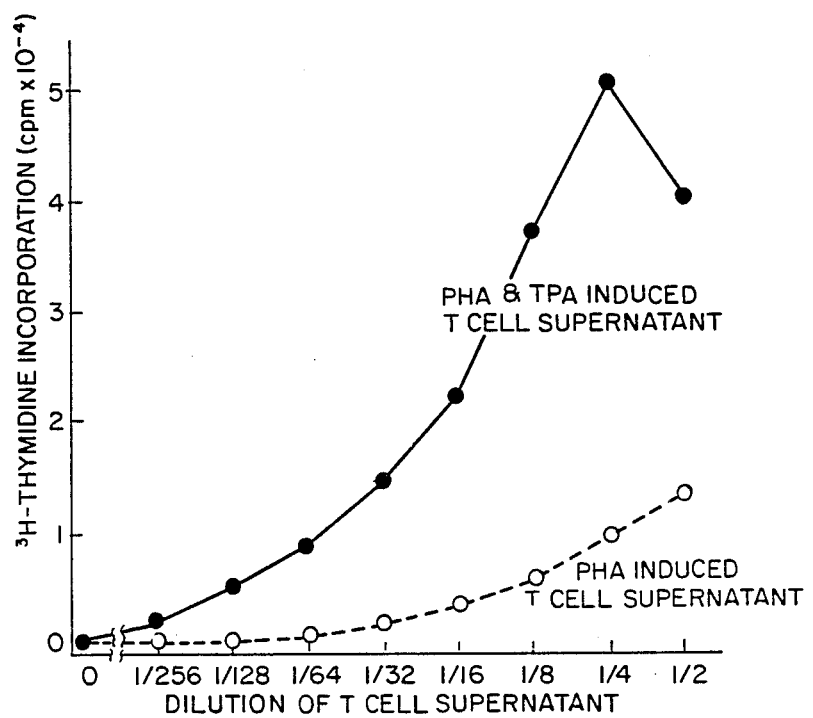
FIG. 4 shows the proliferated response of IL-2 dependent lymphocytes evoked by the cell free supernatant of PHA activated human T lymphocytes and of PHA and TPA activated human T lymphocytes.

FIG. 4 shows the induced proliferation of an IL-2 dependent long term alloreactive clone by the supernatants of T cells activated by PHA and TPA or by PHA alone. The effect of the PHA and TPA-induced T cell supernatant is greater than that of one induced by PHA alone.

After the PBM's were stimulated with PHA and TPA, these inducers and the mouse serum were washed out and the activated T cells were resuspended in a serum-free medium for collection of cell-free products. Using $^3$H-TPA tracer, it was found that although significant amounts of TPA (about 20%) were retained within the cells, less than 1% of the original TPA appeared in the culture supernatant.

Figure 5:
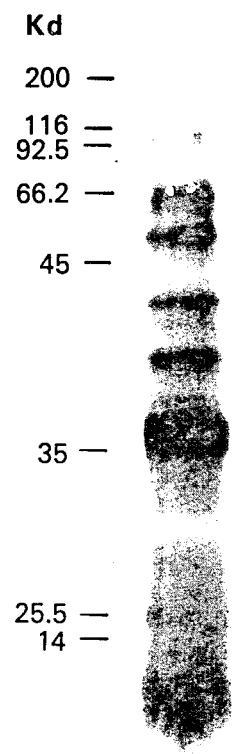
FIG. 5 shows SDS polyacrylamide gel electrophoresis of the cell free products of activated human T lymphocytes.

The cell-free activated T cell supernatant was analyzed chemically. About 100 ug of protein was applied to a lane of 15% acrylamide slab gel. SDS polyacrylamide gel electrophoretic analysis indicated that the supernatant contained molecules predominately in the 10,000 to 80,000 molecular weight range (FIG. 5). IgG and PHA contamination was not detectable in the supernatant. Many conspicuous bands were present, but the nature of the molecules contained therein was not determined.

II. Immunization of mice and monitoring of immune status

CAF1 mice (initially 6 week old females) were injected i.p. with 100 ug, per animal, of the cell-free substance from activated human T cells. Among several immunization protocols tested the best was found to be the following: the first injection was given in complete Freund's adjuvant, the second in incomplete Freund's adjuvant, and all others, including the final boost, in alum precipitate. The second injection was 3 weeks after the first and all others were 2 weeks apart. The final boost was given 7 days before the mice were sacrificed to obtain spleens for hybridization. Three days after the final boost, 1 ml of a supernatant from PHA/TPA-activated CAF1 mouse spleen cells was injected intraperitoneally.

The supernatant from activated spleen cells was prepared in essentially the same way as the supernatant from activated T cells except that cell and reagent concentrations were different. Spleen cells of CAF1 mice were suspended at $5 \times 10^6$ cells/ml in a medium containing 1% CAF1 mouse serum and PHA(2 ug/ml). The cells were incubated for 44 hours and the TPA (10 ug/ml) was added. At 48 hours, the cells were removed from the medium, washed and resuspended in a medium without serum supplement. Sixteen hours thereafter the medium was collected, concentrated 20-fold, and then injected into the mice.

Figure 2:
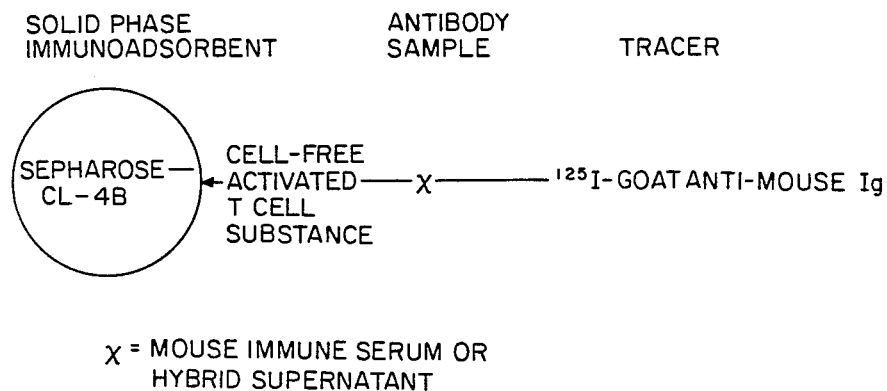
FIG. 2 is a schematic depiction of the solid phase radioimmunoassay used to monitor the immune status of mice and to screen hybrids for production of antibodies reactive with products of activated T lymphocytes.

The immune status of the injected mice was assessed by solid phase radioimmunoadsorbent assay, which was essentially the same as that used for screening hybrid cells (infra). FIG. 2 is a schematic depiction of the assay. The assay measured the reactivity of immune serum to the activated T cell substances conjugated to CNBr-activated Sepharose 4B (20 ug protein per ml of beads). After 4–5 injections, the serum of some mice showed a titer of about ten thousand. (The titer was defined as the factor of dilutions that gave a signal twice that of the background level). These mice were selected for spleens. At this time, the mice were given a final injection prior to removing the spleens for fusion.

Figure 6:
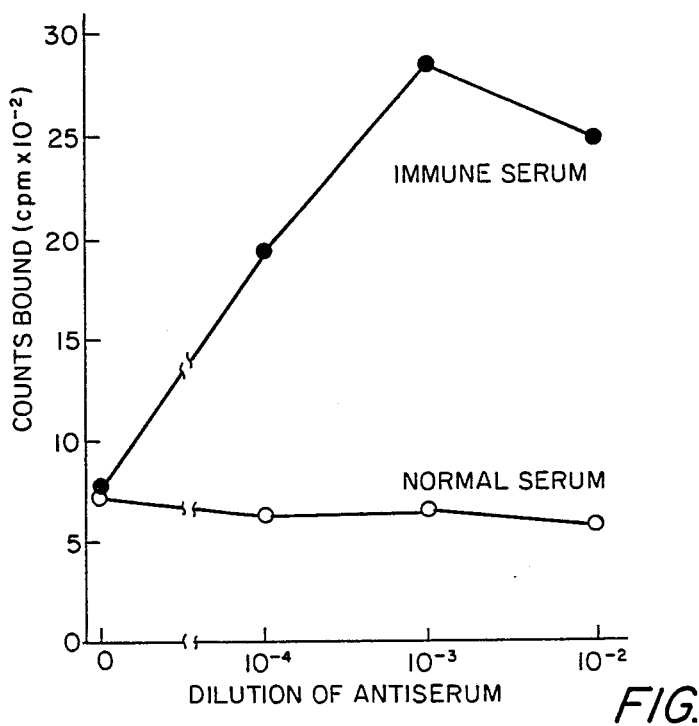
FIG. 6 shows the reactivity of mouse immune serum to cell free products of activated T lymphocytes. The assay was the same as that depicted in FIG. 2.

One obvious property of the antiserum was its reactivity with the cell-free activated T cell substance. In fact, the solid phase radioimmunoassay, which was used to monitor the immune status of the mice, was based on the level of this reactivity. As indicated in FIG. 6, after 5 injections, the titer of the antiserum was over 10,000. The titer was defined as the dilution factor that yields a signal twice that of the background level.

Figure 7:
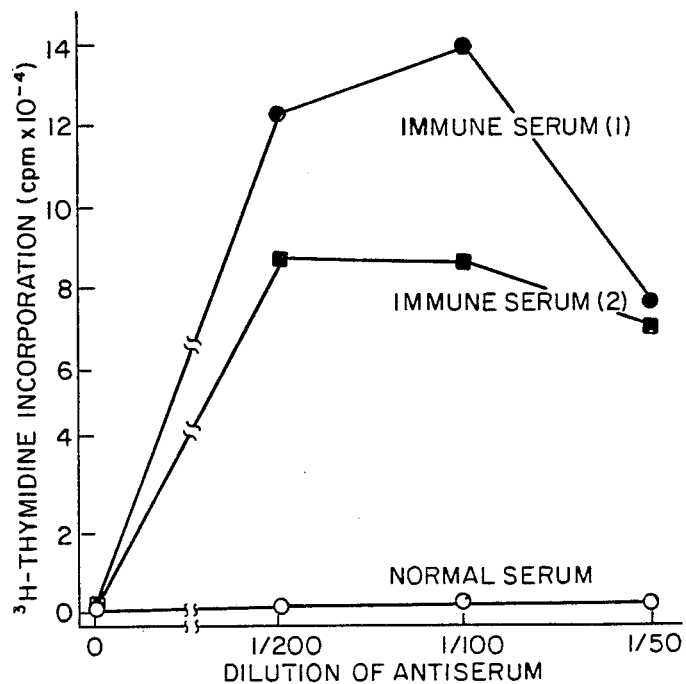
FIG. 7 shows the mitogenic effects of mouse immune serum on human mononuclear cells.

Further, the antiserum was mitogenic to normal human PBM's. FIG. 7 shows the results of a proliferation assay performed as in FIG. 3. The culture medium was RPMI-1640 supplemented with 10% fetal calf serum. Cells were incubated with immune serum for three days. As shown in FIG. 7, the titer of this activity reached a few hundred. This mitogenic activity was not due to "OKT3-like" antibodies, (See Kennett, R. H. (1980) In: *Monoclonal Antibodies (Hybridomas: A New Dimension in Biological Analyses*, eds. R. H. Kennett, T. J. McKearn, K. B. Bechtol (Plenum Press, NY) p. 365.) because unlike the OKT3 antibody, the activity of the antiserum was not inhibited by human serum.

Figure 8:
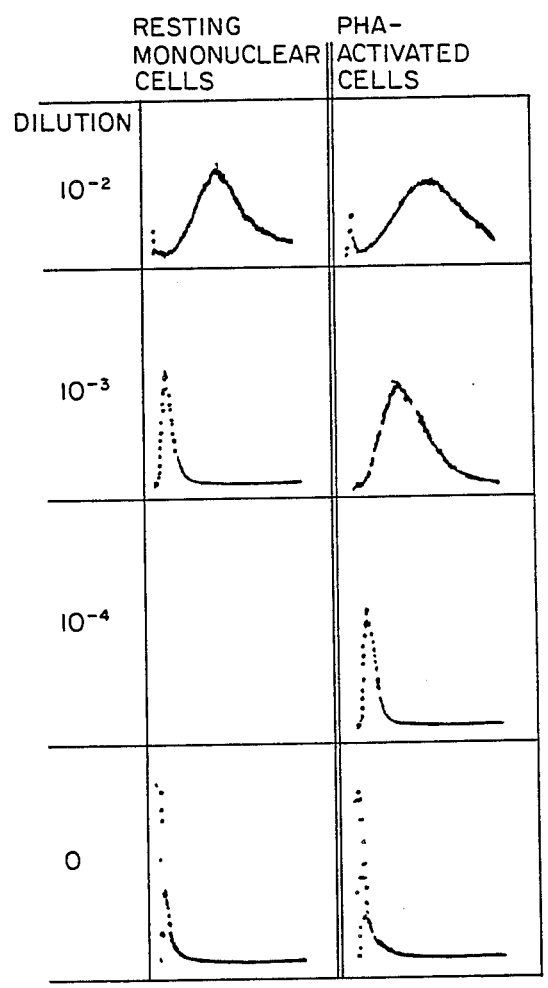
FIG. 8 shows the reactivity of mouse immune serum with cell surface antigens of PHA-activated and resting human mononuclear cells.

Also, the antiserum had appreciable reactivity with cell surface components of PHA-activated blasts and fresh PBM's. FIG. 8 shows flow cytometric analysis of reactivity of immune serum with cell surface antigens of PHA activated and resting mononuclear cells. The activated PBM's were stimulated with PHA (1 ug/ml) in culture for three days. For flow cytometric analysis, the cells were incubated with dilutions of antiserum and stained with FITC-goat anti(mouse Ig) antibody.

This reactivity was not anticipated because the T cell supernatant was filtered through a 0.22 u filter to remove cell debris before use as an immunogen. As shown in FIG. 8, the reactivity is more pronounced with activated blasts than with fresh PBM's. Two possible explanations for the presence of cell surface antigens in the T cell supernatant are that these antigens are shed or secreted or that the membranes of some dead cells are broken down into minute particles.

III. Preparation of hybrids

Spleens from two mice were used for each fusion. Spleen cells and 6-thioguanine-resistant (HGPRT-deficient) NS-1 myeloma cells were hybridized with polyethylene glycol as described. Kennett, R. H. (1980 In: *Monoclonal Antibodies (Hybridomas: A New Dimension in Biological Analyses*, eds. E. H. Kennett, T. J. McKearn, and K. B. Bechtol (Plenum Press, NY), p. 365; Chang, T. W. and N. T. Chang (1982) In: *Genetic Engineering Techniques: Recent Developments*, eds. P. C. Huang, T. T. Kuo, and R. Wu (Academic Press, NY), p. 299. In brief, the spleen cells and myeloma cells were mixed at 5:1 to 10:1 in serum-free medium, and spun down to remove the supernatant. The pelleted cells were loosened and treated with 1 ml of warm 35% polyethylene glycol (M.W. 1000, Baker Chem. Co., Phillipsburg, NJ) for 5 min. During this time, the cells were spun at 600 rpm to increase contact. After the polyethylene glycol was diluted slowly to 15 ml with medium over a period of 5 minutes, the supernatant was removed by centrifugation and the cells were suspended at $2 \times 10^6$/ml in DMEM with 15% fetal calf serum in petri dish. On the next day, additional medium and hypoxanthine, thymidine, and aminopterin were added, and the cells were distributed into the wells of $8 \times 12$ microtiter plates at $2 \times 10^5$ spleen cells per 200 ul per well. Routinely, 50–90% of the wells had growing hybrids.

IV. Screening and characterization of hybrids

Because the serum from immunized mice was found to be reactive with cell-free, cell-surface, and intracellular components of activated T cells, the culture supernatants of hybrids were tested with combinations of the following methods: (1) radioimmunoassay as shown in FIG. 2, to test for reactivity with the cell-free substances of activated T cells; (2) fluorescence flow cytometric analysis with FACS IV (Becton-Dickinson, Mountain View, CA) using live PHA-activated mononuclear cells, to test for reactivity with cell surface antigens (FITC-labelled goat anti-(mouse IG) antibody was used as the fluorescence tracer); and (3) the same method as (2) with formaldehyde-fixed, acetone-permeated PHA-activated blasts, (Vilcek, J. et al. (1980) In: *Biochemical Characterization of Lymphokines*, eds. A. L. DeWeck, F. Kristensen, and M. Landy (Academic Press, NY), p. 323) to detect reactivity with intracellular components.

The radioimmunoassay was prepared as follows: Cell-free products recovered from the activated T cell supernatant were conjugated to Sepharose-4B beads. For routine assays, the protein concentration in Sepharose-4B beads was 20 ug per ml. The beads were post-coated with 5% bovine serum albumin. For each determination, 50 ul beads was incubated with 100 ul hybrid supernatant (or serum dilutions) for 2 hours at room temperature. After washing, the beads were then incubated with 50,000 cpm of $^{125}$I-goat anti-(mouse Ig) antibody (specific activity about 5000 cpm/ng) for 2 hours. They were then washed and counted for $^{125}$I.

These tests served only as the initial screenings to sort out hybrids of potential interest. Further analyses of the antibodies and the antigens that they recognized have been performed, including studies on the distribution of antigen on various subpopulations of normal leukocytes, culture cell lines of various origins, and fresh and frozen human tissues, and studies on the effects of the monoclonal antibodies on various immune activities in vitro.

More than eighty hybrids out of 4000–5000 screened were found to be reactive with the products of activated PBM's. Since not all the screening assays were used to test all hybrids, the actual number of hybrids that were reactive with the immunogen should be higher. Table 1 lists the hybrids that have been cloned and stabilized.

The monoclonal antibodies can be grouped into several categories with respect to target specificities: (1) cell surface, (2) intracellular, and (3) cell-free antigens. Some of the monoclonal antibodies exhibit properties of the antisera, that is: (1) reactivity with T cells, (2) reactivity with cell-free T-cell substance conjugated to Sepharose 4B beads, and (3) ability to induce proliferation of freshly isolated PBM's.

TABLE I

Target antigen specificity of monoclonal antibodies prepared against activated human T cell supernatant substance.[a]

| Hybrid Designation | Cellular Location of Antigen | Nature of Antigen |
|---|---|---|
| CF1 | Cell surface | Proliferation-associated[b] |
| 2 | " | " |
| 6 | " | " |
| 3 | " | Ia-related[b] |
| 7 | " | " |
| 4 | Intracellular | Microfilament element[c] |
| 8 | " | Undetermined |
| 11 | " | " |
| 12 | " | Nuclear[c] |
| 13 | " | Nuclear[d] |
| 5 | Cell-free | Undetermined |
| 14 | " | " |
| 15 | " | " |
| 16 | " | " |
| 17 | " | " |

[a]The group (CF5, 14, 15, 16, and 17) that react with cell-free components in activated T cell supernatant are not positive in immunofluorescence staining assays with live or permeated PHA-activated cells.
[b]Information from Dr. T. Cotner, University of Washington, Seattle, WA, and Dr. A. Bhan, Massachusetts General Hospital, Boston, MA.
[c]Results from collaborative research with Dr. L. B. Chen, Sidney Farber Cancer Center, Boston, MA.

As indicated in the table, the CF-1 hybrid produces a monoclonal antibody which is specific for a cell-surface antigen (CF-1 antigen) associated with proliferation of human cells. The monoclonal anti-CF-1 antibody and the CF-1 antigen are described in greater detail in U.S. patent application Ser. No. 574,916, Applicants T. W. Chang and D. Shealy, filed concurrently herewith, the teachings of which are hereby incorporated by reference. The antigen displays a unique pattern of cellular distribution; it is expressed by activated human lymphocytes but not by resting human lymphocytes or resting human monocytes. Importantly, the antigen is expressed by proliferating human cells such as tumor cells, but not by nonproliferating human cells. As a consequence of this, monoclonal antihuman CF-1 antibody is useful in a number of diagnostic and therapeutic methods as set forth in the aforementioned patent application.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A method of enhancing mitogen-induced proliferation of human T lymphocytes comprising maintaining said lymphocytes in a medium supplemented with mouse serum while exposing the lymphocytes to a mitogen.
2. A method of preparing an immunogenic cell-free supernatant from mitogen activated human T lymphocytes, comprising as the dominant immunogenic substances in mice, products of activated human T lymphocytes, comprising the steps of:
   a. suspending human T lymphocytes in a first mammalian cell culture medium supplemented with mouse serum;
   b. adding a mitogen to the medium;
   c. culturing the T lymphocytes for a period of time and under conditions which support mitogen induced activation of the lymphocytes;
   d. thereafter adding a phorbol ester to the medium to enhance T lymphocyte activation;
   e. further culturing the cells;
   f. separating the lymphocytes from the first medium;
   g. resuspending the lymphocytes in a second mammalian cell culture medium which medium either contains mouse serum or is serum free;
   h. culturing the cells to allow accumulation of secretory products of the activated T cells in the medium; and
   i. separating the medium from the lymphocytes to obtain said cell-free supernatant.
3. A method of claim 2, further comprising the step of washing the cells before resuspension in the second medium.
4. A method of claim 2, wherein said first medium is supplemented with about 0.06 to about 4% mouse serum.
5. A method of claim 2, wherein the mitogen is phytohaemagglutinin A.
6. A method of claim 5, wherein the phorbol ester is 12-O-tetradecanoyl phorbol 13-acetate.
7. A method of claim 6, wherein the final concentration of the added 12-O-tetradecanoyl phorobol 13-acetate is from about 2 to about 10 ng/ml.
8. A method of claim 7, wherein the 12-O-tetradecanoyl phorbol 13-acetate is added to the first medium about 40 hours after the addition of PHA.
9. A method of claim 8, wherein the lymphocytes are separated from the first medium about 4 hours after the addition of 12-O-tetradecanoyl phorbol 13-acetate.
10. A method of claim 9, wherein the lymphocytes are separated from the second medium after about 64 hours.
11. A method of claim 1, wherein the medium is supplemented with about 0.06% to about 4% mouse serum.
12. A method of claim 1, wherein the mitogen is phytohemagglutinin A.
13. A method of preparing an immunogenic supernatant from mitogen-activated human T lymphocytes, which supernatant comprises, as dominant immunogenic substances in mice, products of activated human T lymphocytes, comprising the steps of:
   a. adding human T lymphocytes to a cell culture medium supplemented with about 1% mouse serum;
   b. adding phytoemagglutinin A (PHA) to the medium at a concentration of about 1 ng/ml;
   c. culturing the T lymphocytes under conditions which support PHA-induced activation;
   d. adding 12-O-tetradecanoyl phorbol-13-acetate to the medium at a concentration of 1–10 ng/ml;
   e. further culturing the T lymphocytes under conditions which support PHA induced activation;
   f. separating the T lymphocytes from the medium;
   g. adding the T lymphocytes to a serum-free cell culture medium;
   h. culturing the T lymphocytes to allow secretory products to accumulate in the medium; and
   i. removing the T lymphocytes from the medium to obtain the T lymphocyte supernatant.

* * * * *